US011684595B2

(12) United States Patent
Abrams

(10) Patent No.: US 11,684,595 B2
(45) Date of Patent: Jun. 27, 2023

(54) CHARACTERIZATION OF THE ORAL MICROBIOME FOR THE NON-INVASIVE DIAGNOSIS OF BARRETT'S ESOPHAGUS

(71) Applicant: The Trustees of Columbia University in the City of New York, New York, NY (US)

(72) Inventor: Julian Abrams, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 653 days.

(21) Appl. No.: 16/500,195

(22) PCT Filed: Apr. 9, 2018

(86) PCT No.: PCT/US2018/026689
§ 371 (c)(1),
(2) Date: Oct. 2, 2019

(87) PCT Pub. No.: WO2018/187802
PCT Pub. Date: Oct. 11, 2018

(65) Prior Publication Data
US 2020/0061000 A1    Feb. 27, 2020

Related U.S. Application Data

(60) Provisional application No. 62/483,099, filed on Apr. 7, 2017.

(51) Int. Cl.
*A61K 31/155*       (2006.01)
*A61K 35/741*       (2015.01)
*C12Q 1/686*        (2018.01)
*C12Q 1/6886*       (2018.01)
*C12Q 1/689*        (2018.01)
*A61K 9/00*         (2006.01)
*A61K 35/00*        (2006.01)

(52) U.S. Cl.
CPC .......... *A61K 31/155* (2013.01); *A61K 35/741* (2013.01); *C12Q 1/686* (2013.01); *C12Q 1/689* (2013.01); *C12Q 1/6886* (2013.01); *A61K 9/006* (2013.01); *A61K 2035/115* (2013.01)

(58) Field of Classification Search
CPC ...................................................... A61K 31/155
USPC ........................................................ 514/635
See application file for complete search history.

(56) References Cited

U.S. PATENT DOCUMENTS

| | | | |
|---|---|---|---|
| 7,530,948 B2 | 5/2009 | Seibel et al. | |
| 8,389,792 B2 | 3/2013 | Glimcher et al. | |
| 9,603,876 B2 | 3/2017 | Blaser et al. | |
| 2010/0074872 A1 | 3/2010 | Blaser et al. | |
| 2012/0142542 A1 | 6/2012 | Raftery et al. | |
| 2014/0031258 A1 | 1/2014 | Meltzer et al. | |
| 2016/0220675 A1 | 8/2016 | Abrahmsohn | |

FOREIGN PATENT DOCUMENTS

| | | |
|---|---|---|
| WO | 2010/115077 A2 | 10/2010 |
| WO | 2016/172657 A2 | 10/2016 |

OTHER PUBLICATIONS

Modiano N, Gerson LB. Barrett's esophagus: Incidence, etiology, pathophysiology, prevention and treatment. Therapeutics and Clinical Risk Management. 2007; 3(6): 1035-1145.
Bhardwaj et al., Barrett's Esophagus: Emerging Knowledge and Management Strategies Pathology Research International, 2012, vol. 2012, Article ID 814146, 20 pages.
Singh et al., Barrett's Esophagus: Diagnosis, Screening, Surveillance, and Controversies. Gut and Liver. 2007; 1(2): 93-100.
Bremholm et al., Barrett's esophagus. Diagnosis, follow-up and treatment. Danish medical journal. 2012. 59(8), C4499.
Kolbert, C. P.; Persing, D. H., Ribosomal DNA sequencing as a tool for identification of bacterial pathogens. Current Opinion in Microbiology, 1999, 2 (3), 299-305.
Elliott et al. "A non-endoscopic device to sample the oesophageal microbioia: a case-control study," The Lancet Gastroenterology & Hepatology, 2016, vol. 2, Iss. 1, pp. 32-42.
Snider et al. "Potential Role of the Microbiome in Barrett's Esophagus and Esophageal Adenocarcinoma," Digestive Diseases and Sciences, 2016, vol. 61, Issue 8. pp. 2217-2225.
International Search Report and Written Opinion in corresponding PCT Application No. PCT/US2018/026689, dated Jul. 13, 2018.
Gilchrist et al., Barrett's esophagus: diagnosis by double-contrast esophagography, American Journal of Roentgenology, vol. 150, Issue 1, pp. 97-102, 1988.
Luzna et al., Changes of microRNAs-192, 196a and 203 correlate with Barrett's esophagus diagnosis and its progression compared to normal healthy individuals, Diagnostic Pathology, vol. 6, Issue 114, pp. 1-7, 2011.
Macfarlane et al., Microbial Colonization of the Upper Gastrointestinal Tract in Patients with Barrett's Esophagus, Clinical Infectious Diseases, vol. 45, Issue 1, pp. 29-38, 2007.
Pei et al., Bacterial biota in the human distal esophagus, Proceedings of the National Academy of Sciences of the United States of America, vol. 101, Issue 12, pp. 4250-4255, 2004.
Sun et al., Predicting Barrett's Esophagus in Families: An Esophagus Translational Research Network (BETRNet) Model Fitting Clinical Data to a Familial Paradigm, Cancer Epidemiology Biomarkers & Prevention, vol. 25, Issue 5, pp. 727-735, 2016.

(Continued)

*Primary Examiner* — Raymond J Henley, III
(74) *Attorney, Agent, or Firm* — Leason Ellis LLP

(57) ABSTRACT

The present invention relates to noninvasive microbiome analyses of Barrett's esophagus (BE) patients in which changes in the relative abundance of certain bacteria indicate a disease likelihood or pathogenic state. Additional aspects of the present invention relate to manipulating the microbiome to treat or prevent BE and related conditions. Embodiments also include monitoring for development of disease or monitoring treatment for prevention or elimination of disease states.

8 Claims, 7 Drawing Sheets

(56) References Cited

OTHER PUBLICATIONS

NIH Grant #:5P01CA091955-13, "Clinical risk assessment and prediction", Award Notice Date: Jun. 13, 2016, Budget Start Date: Apr. 1, 2016, Budget End Date: Mar. 31, 2017.
NIH Grant #: 5R03CA186218-02, "Randomized placebo-controlled trial of a gastrin receptor antagonist in barretts esophagus", Award Notice Date: Mar. 24, 2016, Budget Start Date: Apr. 1, 2016, Budget End Date: Mar. 31, 2018.
NIH Grant #: 5R21CA178621-02, "Metabolite bioimarkers in the development of esophageal adenocarcinoma", Award Notice Date: Jul. 24, 2014, Budget Start Date: Sep. 1, 2014, Budget End Date: Aug. 31, 2016.
Behrooz Mozaffari Namin et al:"Effect of probiotics on the expression of Barrett's oesophagus biomarkers", Journal of Medical Microbiology, vol. 64, No. 4, Apr. 1, 2015 (Apr. 1, 2015), pp. 348-354.
Database Embase [Online] Elsevier Science Publishers, Amsterdam, NL; Feb. 3, 2015 (Feb. 3, 2015), Starostin, Boris (Correspondence): "Concomitant therapy of gastroesophagea 1 reflux", XP002800669, retrieved from STN Database accession No. 0051726011 abstract & Starostin, Boris (Correspondence): "Concomitant therapy of gastroesophagea 1 reflux", Diseases of the Esophagus, (Sep. 2014) vol. 27, Supp. Suppl. I, pp. 102A. Abstract No. PI.05.02.
Anonymous: "History of Changes for Study: NCT02513784 Trial to Assess the Effects of an Antimicrobial Mouthwash on the Esophageal Microbiome (Mouthwash )", ClinicalTrials.gov Archive, Jul. 25, 2016 (Jul. 25, 2016), pp. 1-3.
Abrams J A:"The microbiome as a potential biomaricer for oesophageal adenocarcinoma", The Lancet Gastroenterology and Hepatology Jan. 1, 2017 Elsevier Ltd Gbr, vol. 2, No. 1, Jan. 1, 2017, pp. 4-6.
Michael May et al: "Emerging Insights into the Esophageal Microbiome", Current Treatment Options in Gastroenterology, vol. 16, No. 1, Jan. 19, 2018 (Jan. 19, 2018), pp. 72-85.
Supplementary Partial European Search Report dated Nov. 2, 2020.

CHARACTERIZATION OF THE ORAL MICROBIOME FOR THE NON-INVASIVE DIAGNOSIS OF BARRETT'S ESOPHAGUS

CROSS REFERENCE TO RELATED APPLICATIONS

The present application claims priority to U.S. Provisional Patent Application Ser. No. 62/483,099 filed Apr. 7, 2017, which is incorporated herein by reference in its entirety.

FIELD OF INVENTION

The present invention relates to noninvasive microbiome analyses of Barrett's esophagus (BE) patients in which changes in the relative abundance of certain bacteria indicate a disease likelihood or pathogenic state. Additional aspects of the present invention relate to manipulating the microbiome to treat or prevent BE and related conditions. Embodiments also include monitoring for development of disease or monitoring treatment for prevention or elimination of disease states.

BACKGROUND

Barrett's esophagus (BE) is a disease characterized by the replacement of the cell tissue lining of the esophagus with cells more similar to those in the intestine, and can be a serious complication of gastroesophageal reflux disease (GERD). The presence of BE confers a 30- to 40-fold increased risk of a person developing esophageal adenocarcinoma (EAC), a serious cancer with a very high mortality. The rate of EAC incidence has increased by an order of magnitude over the last half century, the prognosis for which is grim. A history of acid reflux symptoms (or gastroesophageal reflux disease (GERD)) is the strongest risk factor for BE. However, a major proportion of patients with BE have no history of GERD, and BE itself exhibits no specific symptoms, making a facile screen for the disease especially needed. Currently, the only diagnostic tool available for BE is upper endoscopy and biopsy, an invasive, uncomfortable, involved, and expensive procedure. The increased rate of EAC occurrence and the disease's lack of specific symptoms calls for the development of a non-invasive, facile diagnostic for BE.

SUMMARY

In certain embodiments, the present invention relates to a method for treating or preventing Barrett's esophagus (BE) and related disorders in a mammal comprising applying an oral antimicrobial or antiseptic rinse at least once daily.

In certain embodiments, the present invention relates to a method for detecting or diagnosing Barrett's esophagus (BE) and/or related disorders in a mammal comprising determining the relative abundance of *Veillonella dispar, Streptococcus, Lautropia*, Enterobacteriaceae, and *Lactobacillus* is indicative of BE and/or related disorders, when compared with an oral sample from a healthy control oral sample.

In yet additional embodiments, the present invention relates to a method for monitoring treatment of Barrett's esophagus (BE) and related disorders in a mammal comprising determining the relative abundance of *Veillonella dispar, Streptococcus, Lautropia*, Enterobacteriaceae, and *Lactobacillus* in an oral sample of the mammal, wherein the presence of *Lactobacillus* and/or an increase in the relative abundance of *Veillonella dispar, Streptococcus*, and/or Enterobacteriaceae and/or a decrease in the relative abundance of *Lautropia* is indicative of BE and/or related disorders, when compared with the relative abundance of *Veillonella dispar, Lactobacillus, Streptococcus*, Enterobacteriaceae, and/or *Lautropia* in a healthy control oral sample.

In certain embodiments, the oral sample is indicative of the oral and/or esophageal microbiota.

In additional embodiments, the determining step involves screening bacterial 16S rRNA genes using PCR.

In additional embodiments, the related conditions are selected from the group consisting of esophageal cancer, esophageal adenocarcinoma, gastroesophageal reflux disease (GERD), and indigestion, and eosinophilic esophagitis.

In certain embodiments, the antimicrobial or antiseptic rinse comprises chlorhexidine.

In certain embodiments, the related conditions are selected from the group consisting of esophageal cancer, esophageal adenocarcinoma, gastroesophageal reflux disease (GERD), and indigestion, and eosinophilic esophagitis.

In certain embodiments, the method further comprises administering an effective amount of one or more probiotics or prebiotics.

In certain embodiments, the oral antimicrobial or antiseptic rinse is continued for at least two weeks.

In certain embodiments, the oral antimicrobial or antiseptic rinse is continued until a desired esophageal and/or salivary microbiome is achieved.

In yet additional embodiments, the present invention relates to a method of treating Barrett's esophagus (BE) and/or related disorders in a mammal comprising administering to the mammal a therapeutically effective amount of a prebiotic or probiotic composition comprising one or more bacterial strains, wherein the composition (i) stimulates growth and/or activity of bacteria which are under-represented in microbiota of the mammal as compared to healthy subjects and/or (ii) inhibits growth and/or activity of bacteria which are over-represented in microbiota of the mammal as compared to healthy subjects.

In certain embodiments, the related disorders are selected from the group consisting of esophageal cancer, esophageal adenocarcinoma, gastroesophageal reflux disease (GERD), and indigestion, and eosinophilic esophagitis.

In certain embodiments, the bacterial strain contained in the prebiotic or probiotic composition is a live bacterial strain.

In additional embodiments, the prebiotic or probiotic composition further comprises a buffering agent selected from the group consisting of sodium bicarbonate, milk, and yogurt. In certain embodiments the mammal is human. In further embodiments, the microbiota is oral and/or esophageal microbiota and the prebiotic or probiotic composition is administered orally.

BRIEF DESCRIPTION OF THE DRAWINGS

The patent or application file contains at least one drawings executed in color. Copies of this patent or patent application publication with color drawing(s) will be provided by the Office upon request and payment of the necessary fee.

FIG. 1A is a cladogram showing taxonomic differences between all tested patients with BE (n=32) and non-BE controls (n=17). FIG. 1B is a graph showing a receiver operating curve (AUROC=0.90) for a model containing relative abundance of genera *Lautropia, Streptococcus*, and Enterobacteriaceae to distinguish patients with BE (n=32) and non-BE controls (n=17).

FIG. 2 is a graph showing that BE patients had significantly increased relative abundance of *V. dispar* in saliva, esophageal squamous tissue, and BE (vs. cardia in controls, shown in solid bars). This demonstrates that assessment of the oral microbiome can be used to estimate the relative abundance of specific bacteria in the esophagus, and in turn determine presence or absence of disease (such as BE).

FIG. 4A shows the results of linear discriminant effect size (LEfSe) analysis, comparing the relative abundance of taxa in the salivary microbiome pre- vs. post-treatment in the chlorhexidine arm. FIG. 4B shows the results of LEfSe analysis at follow-up comparing the chlorhexidine vs. no treatment arms. These results demonstrate that treatment with chlorhexidine mouth rinse causes distinct shifts in the oral microbiome.

DETAILED DESCRIPTION

Figure 1A:
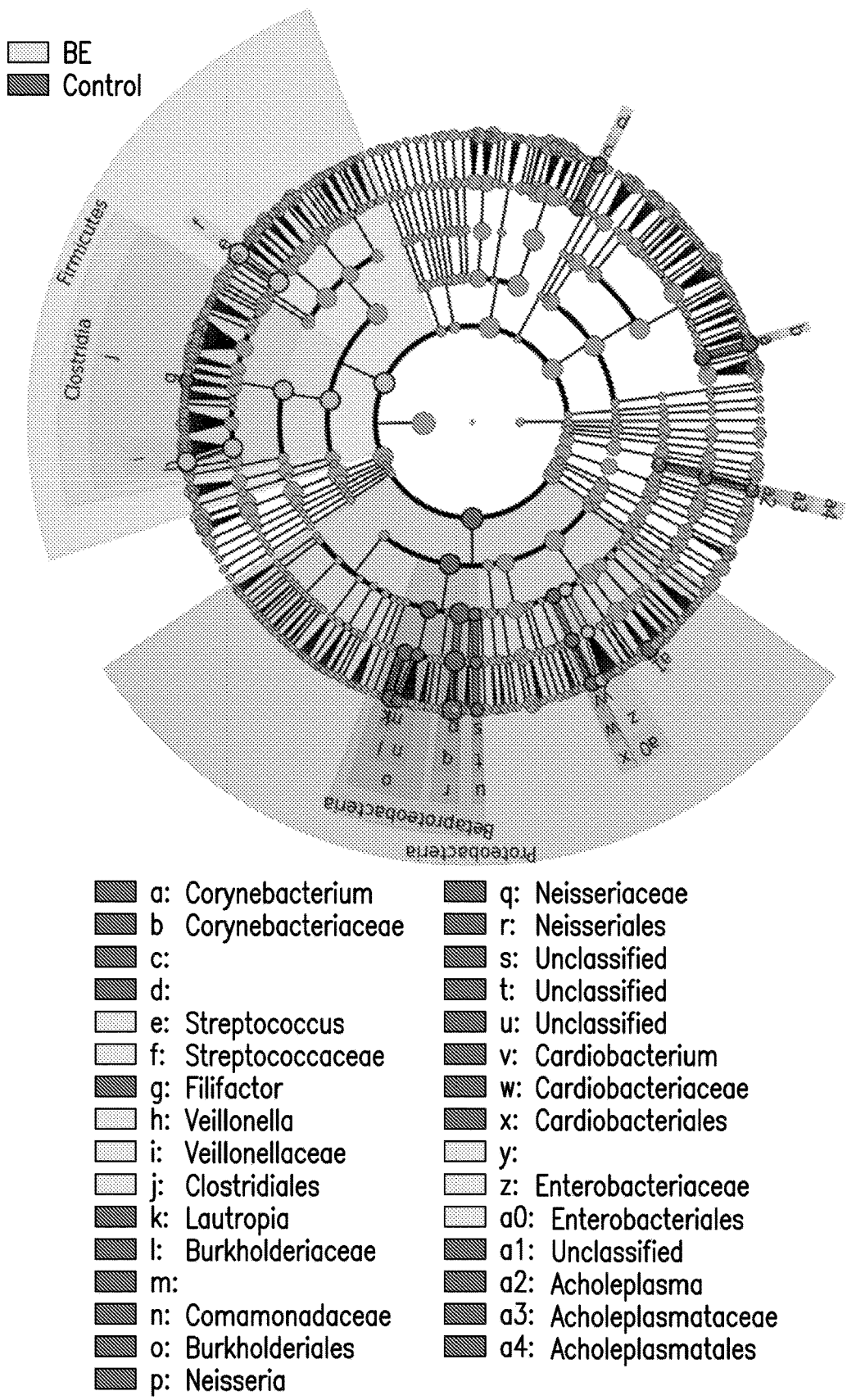
FIGS. 1A-1B are a cladogram and graph distinguishing the oral microbiomes between patients with BE and non-BE controls.

Barrett's esophagus (BE) is a disease characterized by the replacement of the cell tissue lining of the esophagus with cells more similar to those in the intestine, and BE can be a serious complication of GERD. BE increases the risk by 30- to 40-fold of a person of developing esophageal adenocarcinoma (EAC), a serious cancer with a dismal prognosis that's been on the rise over the past 50 years. Embodiments of the present invention provide a uniquely non-invasive diagnostic tool for BE, utilizing the collection of either saliva or an oral swab and the analysis of the oral microbiome. By discriminating between the microbiomes of patients with BE from those without BE, this technology holds significant promise as a potential non-invasive, quick screening test to identify patients with Barrett's esophagus.

The esophageal microbiome is composed of predominantly oropharyngeal flora and is altered in reflux-related conditions including Barrett's esophagus (BE). Changes to the esophageal microbiome may be reflected in the oral cavity, and sampling the oral microbiome thus represents a potential non-invasive method to identify patients with BE. We performed a cross-sectional study to determine whether the oral microbiome is altered in patients with BE.

Aspects of the present invention relate to a diagnostic tool for BE, which provides for analysis of the oral or esophageal microbiome of the patient. Specifically, the present data shows that compared to those without BE, patients with BE exhibited an increased relative abundance of *Veillonella dispar (V. dispar)*, the genus *Streptococcus*, and the family Enterobacteriaceae, as well as decreased relative abundance of the genus *Lautropia*. The present results also show that, using a relative abundance cut-off of 0.1%, the genus *Lactobacillus* was present in some patients with BE, but not present in any of the control patients without BE.

Additionally, the present data shows the oral microbiome to correlate strongly with the esophageal microbiome, allowing this technology to utilize a saliva sample or a simple oral swab to collect the microbiome sample instead of a more invasive sample collection in the esophagus. Thus, the low relative abundance of *V. dispar*, genus *Streptococcus*, and family Enterobacteriaceae, as well as increased relative abundance of genus *Lautropia* and absence of genus *Lactobacillus* distinguishes non-BE from BE. Together, this technology demonstrates that the analysis of the oral microbiome holds significant promise as a potential non-invasive, quick screening test to identify patients with BE.

Definitions

The term "bacteria" encompasses both prokaryotic organisms and archaea present in mammalian microbiota.

The terms "intestinal microbiota", "gut flora", and "gastrointestinal microbiota" are used interchangeably to refer to bacteria in the digestive tract.

Strain Information

*Veillonella dispar*—the bacterial species *Veillonella dispar* (all strains);

*Streptococcus*—the genus *Streptococcus* (inclusive of all species within the genus);

Enterobacteriaceae—the family Enterobacteriaceae (inclusive of all genera and species within the family);

*Haemophilus*—the genus *Haemophilus* (inclusive of all species within the genus);

*Lautropia*—the genus *Lautropia* (inclusive of all species within the genus);

*Lactobacillus*—the genus *Lactobacillus* (inclusive of all species within the genus).

BE "microbiome signature"—a numeric value based on a logistic regression model incorporating relative abundance of various bacterial taxa from a sample (such as saliva, oral swab, or esophageal brushings or gastric cardia brushings).

BE and Related Conditions

Barrett's esophagus is a condition in which tissue that is similar to the lining of the intestine replaces the tissue lining of the esophagus. People with Barrett's esophagus may develop a rare cancer called esophageal adenocarcinoma. Related conditions include: esophageal cancer, and specifically, esophageal adenocarcinoma, gastroesophageal reflux disease (GERD), and indigestion, and eosinophilic esophagitis. GERD is a digestive disorder that affects the lower esophageal sphincter (LES), the ring of muscle between the esophagus and stomach. Many people, including pregnant women, suffer from heartburn or acid indigestion caused by GERD.

Specific changes in microbiome or microbiota discussed herein can be detected using various methods, including without limitation quantitative PCR or high-throughput sequencing methods which detect over- and under-represented genes in the total bacterial population (e.g., 454-sequencing for community analysis; screening of microbial 16 S ribosomal RNAs (16 S rRNA), etc.), or transcriptomic or proteomic studies that identify lost or gained microbial transcripts or proteins within total bacterial populations. See, e.g., U.S. Patent Publication No. 2010/0074872; Eckburg et al., Science, 2005, 308:1635-8; Costello et al., Science, 2009, 326:1694-7; Orrice et al., Science, 2009, 324:1190-2; Li et al., Nature, 2010, 464: 59-65; Bjursell et al., Journal of Biological Chemistry, 2006, 281:36269-36279; Mahowald et al., PNAS, 2009, 14:5859-5864; Wikoff et al., PNAS, 2009, 10:3698-3703.

The term "probiotic" refers to a substantially pure bacteria (i.e., a single isolate, live or killed), or a mixture of desired bacteria, or bacterial extract, and may also include any additional components that can be administered to a mammal. Such compositions are also referred to herein as a "bacterial inoculant." Probiotics or bacterial inoculant compositions of the invention are preferably administered with a buffering agent (e.g., to allow the bacteria to survive in the acidic environment of the stomach and to grow in the intestinal environment). Non-limiting examples of useful buffering agents include saline, sodium bicarbonate, milk, yogurt, infant formula, and other dairy products.

The term "prebiotic" refers to an agent that increases the number and/or activity of one or more desired bacteria. Non-limiting examples of prebiotics useful in the methods of the present invention include fructooligosaccharides (e.g., oligofructose, inulin, inulin-type fructans), galactooligosaccharides, N-acetylglucosamine, N-acetylgalactosamine, glucose, other five- and six-carbon sugars (such as arabinose, maltose, lactose, sucrose, cellobiose, etc), amino acids, alcohols, resistant starch (RS), and mixtures thereof. See, e.g., Ramirez-Farias et al., Br J Nutr (2008) 4:1-10; Pool-Zobel and Sauer, J Nutr (2007), 137:2580S-2584S.

The term "metagenome" refers to genomic material obtained directly from a subject, instead of from culture. Metagenome is thus composed of microbial and host components.

The terms "treat" or "treatment" of a state, disorder or condition include: (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms.

Therapeutic embodiments described herein include using an antimicrobial or antiseptic mouth rinse to alter the esophageal and/or gastric microbiome in a desired manner, as described further herein and below. A non-limiting example of an antimicrobial mouth rinse includes chlorhexidine mouth rinse (i.e. an antiseptic oral rinse), which effectively reduces levels of many bacteria in the mouth, including anaerobes and species that are not easily cultured, and also has anti-inflammatory effects. It is expected that numerous commercially available antimicrobial ("antiseptic") mouth rinses would be useful in the presently claimed methods. Non-limiting examples include Listerine®, Scope®, Cepacol®, and many others. Another suitable option for an oral rinse would include those described in U.S. Pat. No. 9,084,902. Any suitable antimicrobial and/or antiseptic oral rinse solution can be utilized in the methods described herein.

The benefit to a subject to be treated is either statistically significant or at least perceptible to the patient or to the physician. In certain embodiments, the oral antimicrobial or antiseptic rinse is continued for at least two weeks, but the time frame for such treatment can be any desired time frame. In certain embodiments, the oral antimicrobial or antiseptic rinse is continued until a desired esophageal and/or salivary microbiome is achieved.

In connection with administration of antibiotics, the term "antibiotic treatment" comprises antibiotic exposure.

The term "early in life" refers to the period in life of a mammal before growth and development is complete. In case of humans, this term refers to pre-puberty, preferably within the first 6 years of life.

A "therapeutically effective amount" means the amount of a bacterial inoculant or a compound (e.g., an antibiotic or a prebiotic) that, when administered to a subject for treating a state, disorder or condition, is sufficient to effect such treatment. The "therapeutically effective amount" will vary depending on the compound, bacteria or analogue administered as well as the disease and its severity and the age, weight, physical condition and responsiveness of the mammal to be treated.

When used in connection with antibiotic administration, the term "therapeutic dose" refers to an amount of an antibiotic that will achieve blood and tissue levels corresponding to the minimal inhibitory concentration (MIC) for at least 50% of the targeted microbes, when used in a standardized in vitro assay of susceptibility (e.g., agar dilution MICs; see Manual of Clinical Microbiology, ASM Press).

The term "sub-therapeutic antibiotic treatment" or "sub-therapeutic antibiotic dose" refers to administration of an amount of an antibiotic that will achieve blood and tissue levels below the minimal inhibitory concentration (MIC) for 10% of targeted organisms, when used in a standardized in vitro assay of susceptibility (e.g., agar dilution MICs; see Manual of Clinical Microbiology, ASM Press). Non-limiting examples of useful doses for sub-therapeutic antibiotic treatment include 1-5 mg/kg/day.

The phrase "pharmaceutically acceptable" refers to molecular entities and compositions that are generally regarded as physiologically tolerable.

The term "combination" of a bacterial inoculant, probiotic, analogue, or prebiotic compound and at least a second pharmaceutically active ingredient means at least two, but any desired combination of compounds can be delivered simultaneously or sequentially (e.g., within a 24 hour period).

"Patient" or "subject" refers to mammals and includes, without limitation, human and veterinary animals.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

General Methods

Standard methods in molecular biology are described Sambrook, Fritsch and Maniatis (1982 & 1989 2nd Edition, 2001 3rd Edition) Molecular Cloning, A Laboratory Manual, Cold Spring Harbor Laboratory Press, Cold Spring Harbor, N.Y.; Sambrook and Russell (2001) Molecular Cloning, 3rd ed., Cold Spring Harbor Laboratory Press, Cold Spring Harbor, N.Y.; Wu (1993) Recombinant DNA, Vol. 217, Academic Press, San Diego, Calif.). Standard methods also appear in Ausbel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) Current Protocols in Protein Science, Vol. 1, John Wiley and Sons, Inc., New York). Chemical analysis, chemical modification, post-translational modification, production of fusion proteins, glycosylation of proteins are described (see, e.g., Coligan, et al. (2000) Current Protocols in Protein Science, Vol. 2, John Wiley and Sons, Inc., New York; Ausubel, et al. (2001) Current Protocols in Molecular Biology, Vol. 3, John Wiley and Sons, Inc., NY, N.Y., pp. 16.0.5-16.22.17; Sigma-Aldrich, Co. (2001) Products for Life Science Research, St. Louis, Mo.; pp. 45-89; Amersham Pharmacia Biotech (2001) BioDirectory, Piscataway, N.J., pp. 384-391). Production, purification, and fragmentation of polyclonal and monoclonal antibodies are described (Coligan, et al. (2001) Current Protocols in Immunology, Vol. 1, John Wiley and Sons, Inc., New York; Harlow and Lane (1999) Using Antibodies, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) Current Protocols in Immunology, Vol. 4, John Wiley, Inc., New York).

Example 1

The microbiome of the esophagus is altered in patients with BE, the precursor to EAC. Furthermore, the esophageal microbiome is predominantly made up of bacteria that come from the mouth. Therefore, studying the oral microbiome represents an attractive means to determine whether patients may be at increased risk for EAC.

Figure 1B:
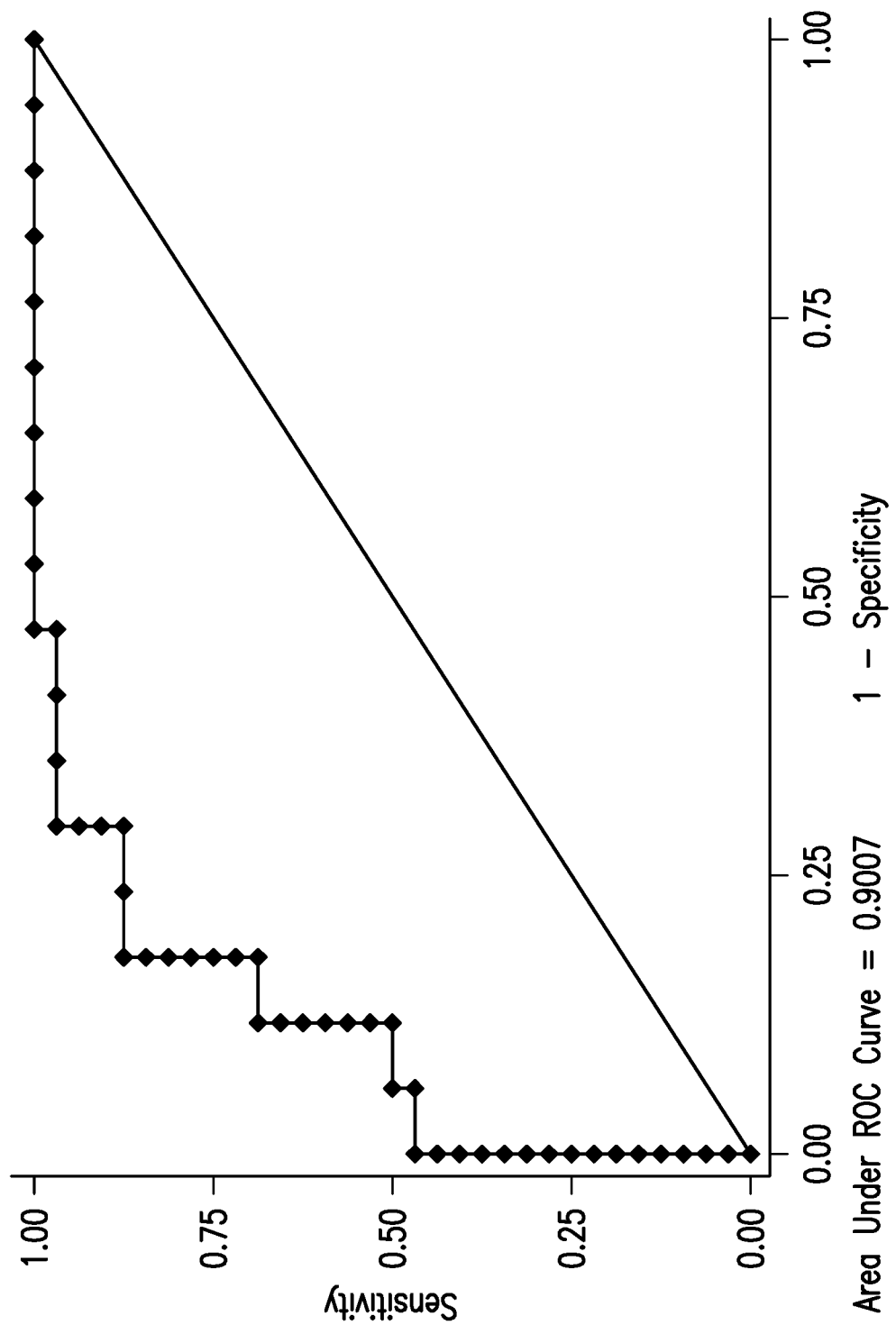

Results: A total of 49 patients were included in the study (control=17, NDBE=16, LGD=6, HGD/EAC=10). There was no significant difference in microbial richness or alpha diversity in saliva comparing all BE patients with controls. There was evidence of significant clustering (all BE vs. controls) based on weighted UniFrac analyses (p=0.03). At the phylum level, the oral microbiome in BE patients had significantly increased relative abundance of Firmicutes (26.9% vs. 14.7%; p=0.005) and decreased Proteobacteria (23.0% vs. 34.5%; p=0.01) compared to controls. There were numerous differences between BE and controls at the taxon level (as shown in FIG. 1A). A model including relative abundance of genera *Lautropia* and *Streptococcus* and family Enterobacteriaceae distinguished BE from controls with 96.9% sensitivity and 70.6% specificity (AUROC 0.90, 95% CI 0.81-0.99; as shown in FIG. 1B). This model remained a significant predictor of BE status after adjustments for age, sex, PPI use, and dietary fat and fiber intake. There was no difference in alpha diversity or in relative abundance of phyla in saliva from patients with HGD/EAC compared to NDBE, but patients with HGD/EAC had increased relative abundance of Enterobacteriaceae and Streptomycetaceae, with decreased Veillonellaceae.

Conclusions: In this cross-sectional study, the oral microbiome in BE patients was markedly altered and could distinguish BE patients with relatively high accuracy. The oral microbiome represents a potential screening marker or "BE microbiome signature" for BE, and future studies in larger and distinct populations are warranted to validate these findings.

TABLE 1

BE microbiome signature

| | BE patients | Non BE Control Patients | Quantitative amounts/or % |
|---|---|---|---|
| *Veillonella dispar* | +++ | +/− | N/D |
| OTU055 *Lactobacillus delbrueckii* | +++ | − | N/D |
| OTU336 *Lactobacillus* sp | +++ | − | N/D |
| OTU726 *Lactobacillus* sp | +++ | − | N/D |

N/D = not determined.

Methods: Patients with and without BE undergoing upper endoscopy were enrolled, with exclusions for recent antibiotic use or prior endoscopic treatment for BE. Demographics, clinical data, and medication usage including proton-pump inhibitors (PPI) were recorded. Dietary fat and fiber intake for each patient was calculated using a validated food frequency questionnaire that assessed intake over the previous month. Saliva samples were collected prior to endoscopy. Subjects were categorized as non-BE controls, non-dysplastic BE (NDBE), low grade dysplasia (LGD), high grade dysplasia (HGD) or esophageal adenocarcinoma (EAC). Samples were analyzed by sequencing the bacterial 16 S rRNA gene. Taxonomic differences between groups were assessed via linear discriminant analysis effect size (LEfSe). Initial comparisons were made between all BE patients (with or without dysplasia/EAC) vs. controls ('screening'), and subsequently between NDBE vs. HGD/EAC ('surveillance').

Detection, Diagnostic and Treatment Benefits:
  Uses a saliva sample or an oral swab to collect a sample of the patient's microbiome;
  Relies on the strong correlation of oral and esophageal microbiomes in order to analyze the oral microbiome instead of having to more invasively collect an esophageal microbiome sample to analyze;
  Assesses the relative abundance of *Streptococcus*, *Lautropia*, Enterobacteriaceae, *V. dispar* and *Lactobacillus* in the patient and compares it to the relative abundance of these organisms in non BE controls;
  Offers a uniquely non-invasive and simple diagnostic test for BE;
  Is a diagnostic tool for diagnosing BE by analysis of a patient's oral microbiome;
  Potentially applicable to related conditions including, but not limited to: esophageal cancer, and specifically, esophageal adenocarcinoma, gastroesophageal reflux disease (GERD), and indigestion, and eosinophilic esophagitis.

The following data was identified:
  Within individuals, the oral microbiome correlated strongly with the esophageal microbiome, with high median Spearman rank correlation coefficients between saliva and BE (median rho=0.74) and saliva and squamous esophagus (median rho=0.74). Furthermore, correlation coefficients between saliva and both squamous esophagus and BE were significantly greater than for oral swabs. Thus, the oral microbiome is reflective of the esophageal microbiome, and saliva appears superior to oral swab as a biomarker for BE status.

Figure 2:
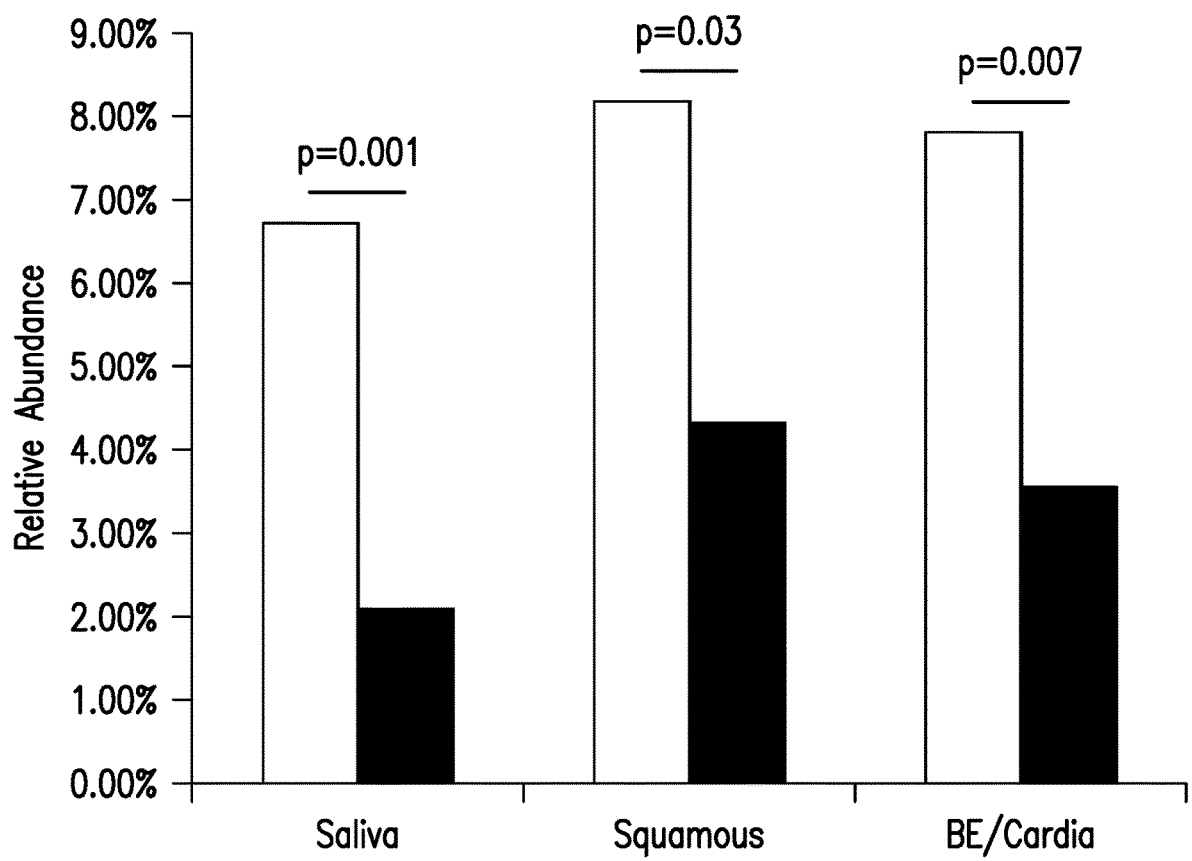
FIG. 2 is a graph showing relative abundance of certain bacteria distinguishing patients with BE vs non-BE controls.

There were significant differences in specific taxa comparing BE patients with controls. Notably, BE patients had increased relative abundance of *Streptococcus* and Enterobacteriacea and decreased relative abundance of *Lautropia* in saliva. A model containing the relative abundance of these three taxa had an area under the ROC of 0.90 for distinguishing BE from non-BE patients. (as shown in FIG. 1B). There was also increased relative abundance of *Veillonella dispar* in saliva, squamous tissue, and BE tissue (FIG. 2). *V. dispar* is associated with inflammatory and invasive processes in oral pathology, and has been found in increased abundance in colon cancers. Thus, bacterial species from the oral microbiome such as *V. dispar* may not only serve as a biomarker for BE, but may also have a pathogenic role in BE and EAC.

Using a relative abundance cut-off of 0.1%, the genus *Lactobacillus* was present in the saliva of certain BE patients but were not present in any of the non-BE control patients.

Together these data demonstrate that analysis of the oral microbiome holds significant promise as a potential noninvasive screening test to identify patients with Barrett's esophagus, or alternatively to rule out the presence of Barrett's esophagus. These results illustrate that low relative abundance of *V. dispar*, genus *Streptococcus*, and family Enterobacteriaceae, as well as increased relative abundance of genus *Lautropia* and absence of genus *Lactobacillus* distinguishes non-BE from BE.

Example 2

Use of an Antimicrobial Mouth Rinse Alters the Microbiome of the Esophagus.

A randomized controlled trial of chlorhexidine antimicrobial mouth rinse study was conducted in patients scheduled to undergo upper endoscopy. It is postulated that the microbiome may play a role in the development of various esophageal and other upper gastrointestinal diseases such as Barrett's esophagus and esophageal cancer. The microbiome of the upper gastrointestinal tract is heavily influenced by migration of bacteria from the mouth via swallowed secretions. Therefore, it stands to reason that altering the oral microbiome can directly impact the microbiome of the esophagus and gastric cardia. Chlorhexidine mouth rinse (i.e. an antiseptic oral rinse) effectively alters levels of many bacteria in the mouth, including anaerobes and species that are not easily cultured, and also has anti-inflammatory effects. A randomized open-label pilot study was performed to test this hypothesis that use of an antimicrobial mouth rinse alters the microbiome of the lower esophagus and gastric cardia.

Study Design

The enrolled subjects were those already scheduled for upper endoscopy for clinical indications.

Subjects were randomized 1:1 to receive 0.12% chlorhexidine mouth rinse or no treatment.

Antimicrobial mouth rinse was used twice daily for two weeks leading up to the endoscopy. The two-week time frame was chosen as a practical end-point for the clinical study, and treatment can be for any desired period of time, i.e. to obtain the desired microbiome mix.

Baseline sample collection: Saliva, oral swab.

Samples collected at follow-up (day of endoscopy): Saliva, oral swab, esophageal brushings, gastric cardia brushings.

Patients scheduled to undergo upper endoscopy were randomized to treatment with chlorhexidine 0.12% mouth rinse or no mouth rinse for two weeks leading up to the endoscopy. Oral samples (swabs and saliva) were collected at baseline and after two weeks. During the endoscopy, brushings of the esophagus and of the gastric cardia were collected to sample the microbiome.

Figure 3A:
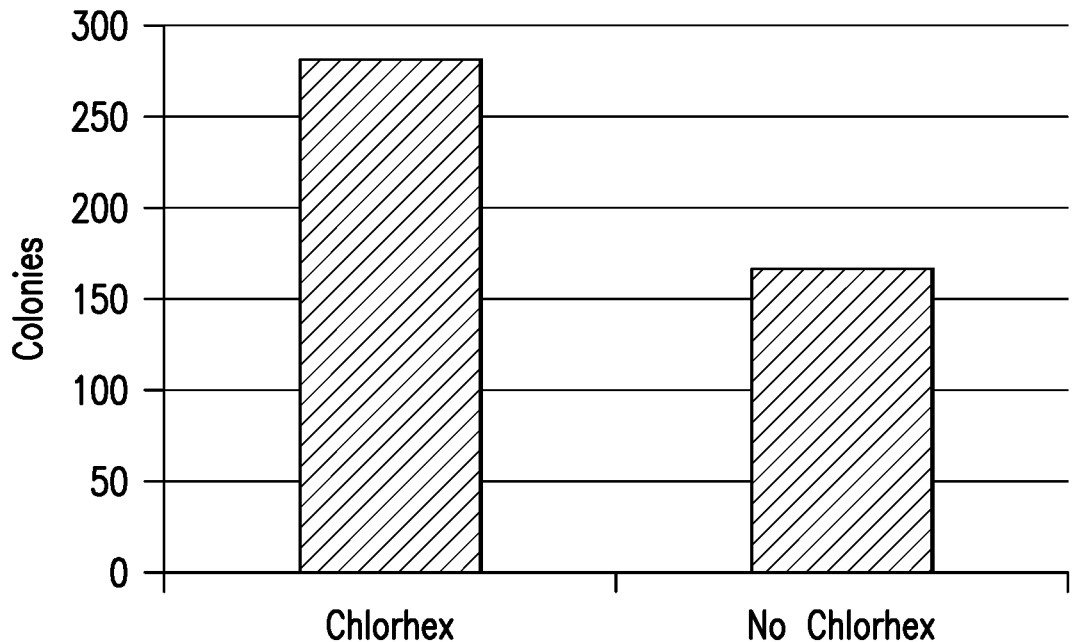
FIGS. 3A-B are graphs showing that patients treated with chlorhexidine had increased numbers of culturable bacteria (both numbers of colonies, FIG. 3A, and CFU/mL, FIG. 3B) in the esophagus, compared to those who did not receive chlorhexidine rinse. This demonstrates that treatment with an antimicrobial mouth rinse can alter the global composition of the esophageal microbiome.
Figure 3B:
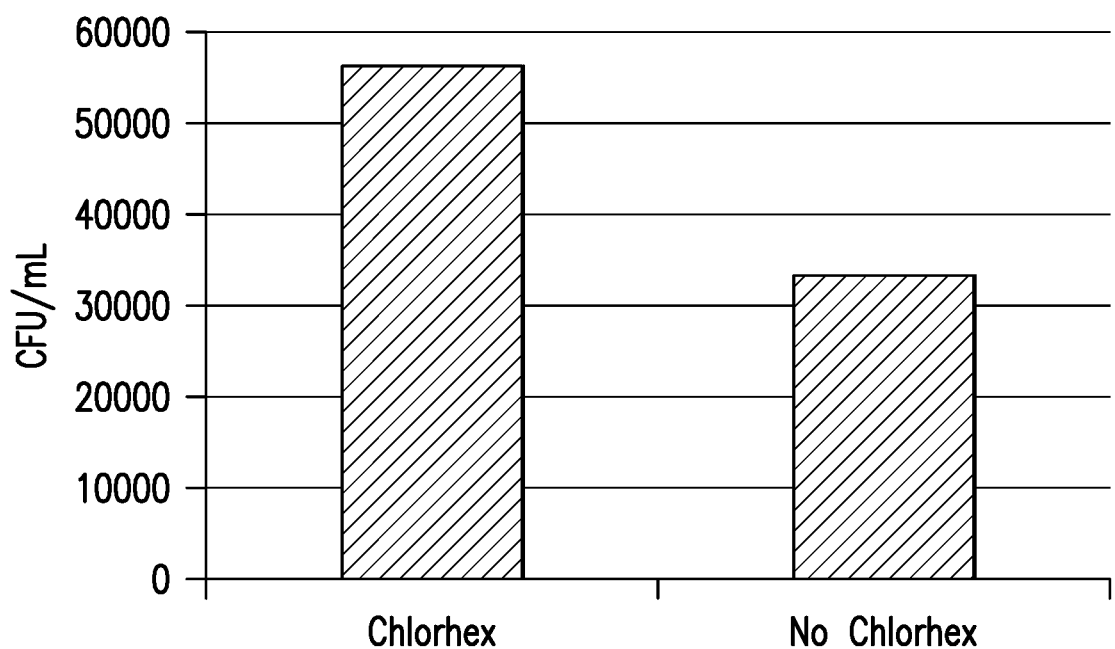

An interim analysis was performed on the esophageal brushings collected during upper endoscopy. Approximately one half of the bacteria in the esophagus can be readily cultured. Thus, it was hypothesized that a change in the amount of culturable bacteria (either increased or decreased) would reflect a change in the proportion of culturable:nonculturable bacteria in the esophagus. Samples from the first 14 subjects (8 controls not using mouth rinse, 6 subjects using chlorhexidine mouth rinse) were collected, and solutions were prepared from these samples. The samples were then plated onto trypticase soy agar (TSA) plates with 5% sheep blood and incubated for 18 hours at 37° C. The patients who were treated with mouth rinse had a 68% increase in growth of culturable bacteria compared to those in the arm not receiving mouth rinse (see Table 2 and FIGS. 3A-B).

These findings strongly suggest that an antimicrobial/antiseptic mouth rinse directly alters the composition of the esophageal microbiome. Therefore, use of an antimicrobial mouth rinse represents a novel mechanism both: 1) to treat esophageal diseases that are influenced by the local microbiome, and 2) to prevent esophageal diseases that are influenced by the local microbiome including: BE, esophageal cancer, and specifically, esophageal adenocarcinoma, gastroesophageal reflux disease (GERD), and indigestion, and eosinophilic esophagitis.

TABLE 2

Mean (SE) number of colonies and CFU/mL from esophageal brushings collected at endoscopy in subjects pre-treated with chlorhexidine (n = 6) compared to no chlorhexidine (n = 8).

|  | Chlorhexidine | No chlorhexidine |
| --- | --- | --- |
| Colonies | 282 (213) | 167 (91) |
| CFU/mL | 56,433 (42,654) | 33,475 (18,173) |

CFU, colony forming units

Example 3

Randomized Controlled Trial of an Antimicrobial Mouth Rinse to Alter the Esophageal Microbiome—16 S Sequencing Data As described above, it is expected, based on the present data that bacteria in the esophagus may play a role in esophageal disease pathogenesis. Further analysis of the samples from the trial was performed utilizing 16 S sequencing data to further characterize the oral and esophageal microbiome changes.

Analyses

16 S rRNA gene sequencing was performed on all of the biosamples. The V3-V4 hypervariable region for all samples was sequenced using the Illumina HiSeq 2500 in Rapid Mode with 2×300 bp read length (Illumina, San Diego, Calif.). The Greengenes reference database was used. Taxonomic units were clustered at 97% sequence similarity using USEARCH and taxonomic assignments were made using mothur. A phylogenetic tree of the contigs was generated with FastTree version 2.1.7.

In order to determine whether chlorhexidine alters the oral microbiome, a comparison of microbiome composition from saliva was performed, comparing baseline with follow-up, in both the treatment and no treatment arms. Additional comparisons were made of saliva between the treatment and no treatment arms at follow-up.

In order to determine whether chlorhexidine alters the esophageal microbiome, a comparison of the microbiome composition from esophageal samples was performed, comparing the treatment and no treatment arms.

These experiments were designed to determine whether the chlorhexidine-induced changes to the microbiome were similar in the mouth (e.g. saliva samples) and in the esophagus.

Results—Salivary Microbiome

Figure 4A:
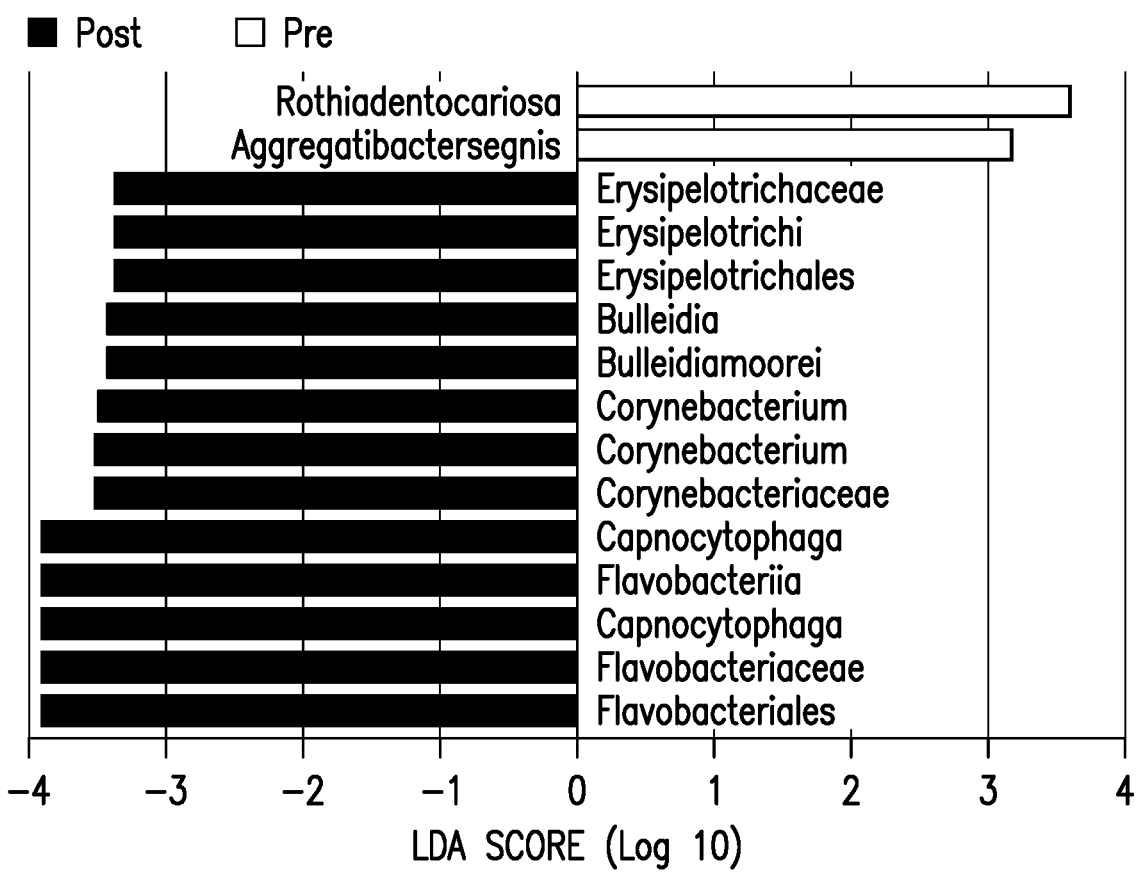
FIGS. 4A-B are graphic analyses of results in the salivary microbiome in control and treated patient groups.
Figure 4B:
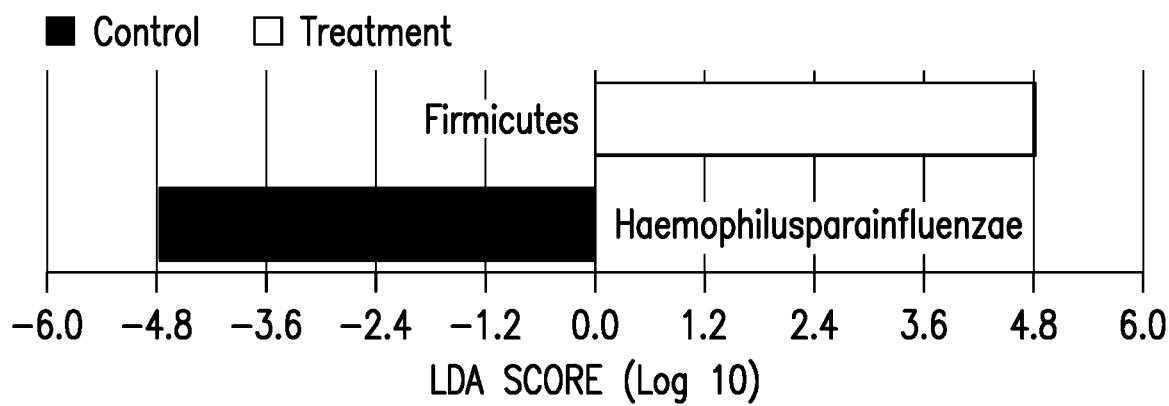

There were no differences between the treatment and control arms at baseline. No taxonomic changes were seen in the control (no mouthwash) group, comparing baseline to follow-up. Numerous taxa were altered after 2 weeks' treatment with chlorhexidine compared to baseline (FIG. 4A). At follow-up, large differences were seen between chlorhexidine and no treatment in phylum Firmicutes and species *Haemophilus parainfluenzae* (FIG. 4B).

Results—Esophageal Microbiome

Figure 5:
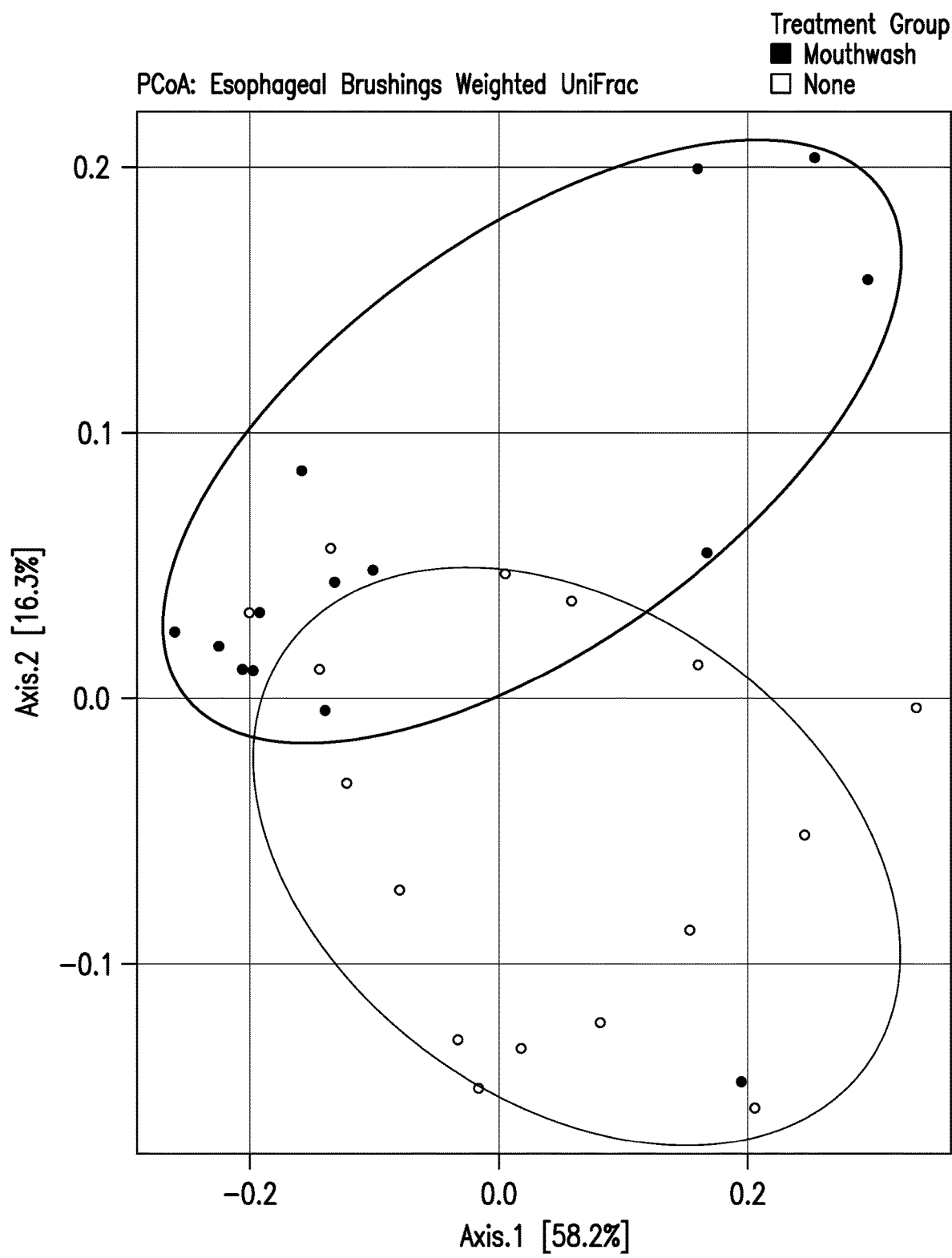
FIG. 5 is a graph showing the beta diversity analyses that illustrates significant clustering by treatment group of the esophageal microbiome.
Figure 6:
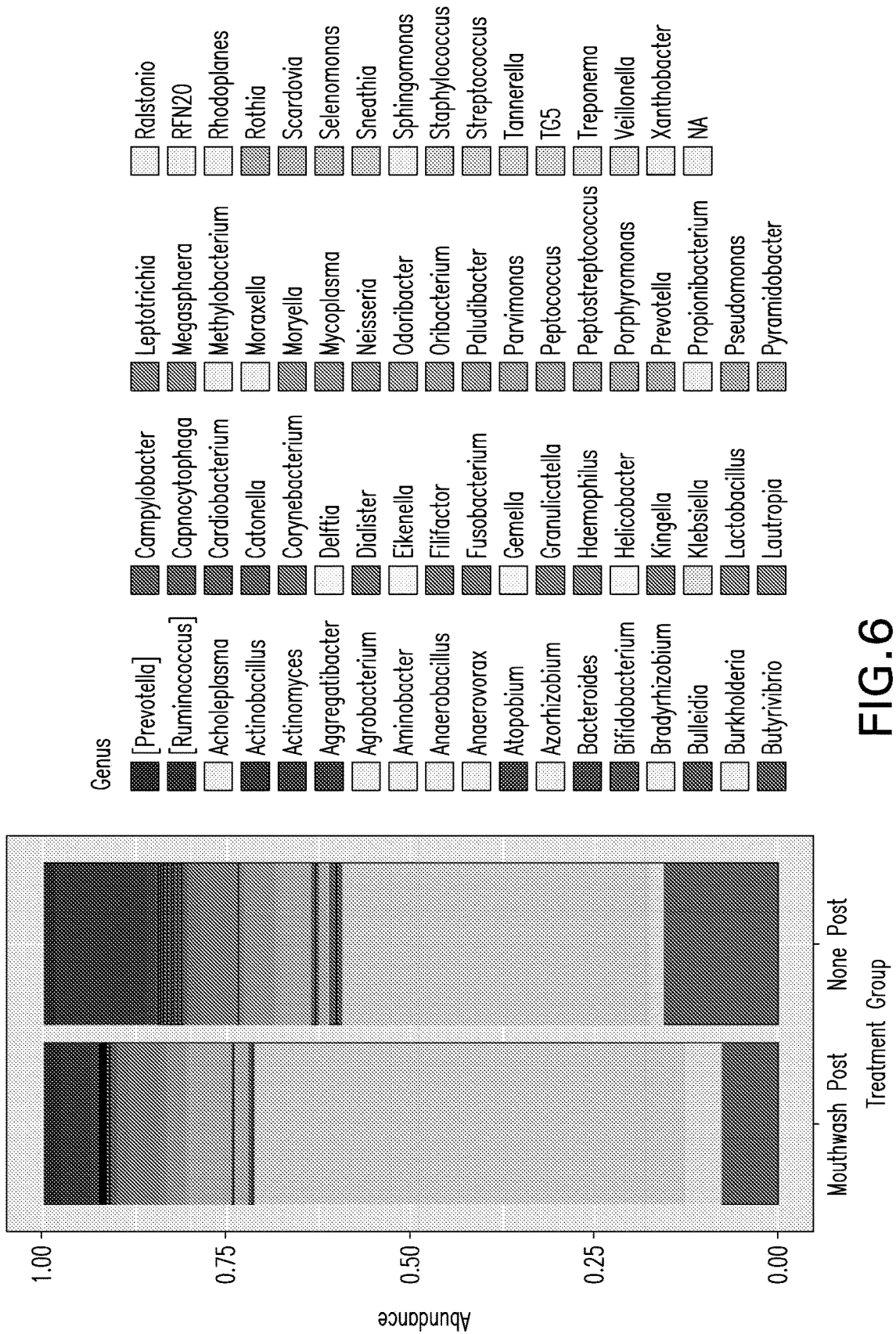
FIG. 6 shows the Taxonomic profiles by treatment group of the esophageal microbiome. This demonstrates that treatment with an antimicrobial mouth rinse induces shifts in the relative abundance of specific taxa in the esophagus, and that these changes mirror those changes seen in the oral microbiome.

The esophageal microbiome was markedly distinct in patients treated with chlorhexidine mouth rinse compared to patients receiving no treatment (FIGS. 5-6). FIG. 5 shows significant clustering by treatment group seen on beta diversity analysis.

Additionally, there was significantly decreased relative abundance of *Haemophilus* in the chlorhexidine mouth rinse arm, as well as increased *Streptococcus* and numerous other altered taxa (FIG. 6). All of the significant esophageal microbiome alterations in the chlorhexidine arm were also observed in the salivary microbiome.

Additional analyses will include RNA-seq analysis of the esophageal biopsies, which will allow for determination of whether chlorhexidine treatment also alters esophageal tissue gene expression. This finding would strongly support a pathogenic role for bacteria in the esophagus, as well as further supporting therapeutic applications for antimicrobial mouth rinse to alter esophageal disease risk and outcomes.

Trial Conclusions

Treatment with an antimicrobial mouth rinse alters the oral microbiome and the esophageal microbiome, and these changes mirror each other closely. Treatment with an antimicrobial mouth rinse can alter the bacterial make-up of the esophagus, and provides a simple and effective therapy to modify (e.g. decrease) the risks and change the outcomes of esophageal diseases and their progression.

The presently identified correlations of BE with the microbiome (i.e. the presently identified microbiome "BE signature/s") is expected to lead to a non-invasive method for detecting and monitoring, and potentially treating BE and related pathogenic conditions. For pathogenic conditions associated with the identified BE microbiome signatures/s, new treatments could be devised, including adjusting the BE pathogenic or pre-pathogenic microbiome with antibiotics, probiotics, or prebiotics. It is expected that such an approach would modify the oral microbiome, and subsequently the esophageal microbiome, and would lead to improved outcomes both for treatment and prevention of BE and related conditions including: esophageal cancer, and specifically, esophageal adenocarcinoma, gastroesophageal reflux disease (GERD), and indigestion, and eosinophilic esophagitis. Such therapies could be carried out alone or in combination.

Applications of this microbiome analysis as a diagnostic tool could be expanded to search for correlations with other related diseases, such as esophageal cancer, and specifically, esophageal adenocarcinoma, gastroesophageal reflux disease (GERD), and indigestion, and eosinophilic esophagitis.

Additionally, it is also proposed that the present microbiome analysis utilizing a BE microbiome signature could be utilized as a diagnostic evaluation specifically for those discovering they have GERD, as the quick, non-invasive nature of the procedure would warrant the preventative measure in a way that an invasive upper endoscopy cannot justify. The present methods would be generally applicable as a screening tool for many patients and not just to those who have GERD.

Finally, the present microbiome analysis utilizing a BE microbiome signature could be utilized as a monitoring tool for analyzing the progress of any therapeutic, including antibiotic, prebiotic, or probiotic treatments for BE, and potentially related conditions including: esophageal cancer, and specifically, esophageal adenocarcinoma, gastroesophageal reflux disease (GERD), and indigestion, and eosinophilic esophagitis.

INCORPORATION BY REFERENCE

All references cited herein are incorporated by reference to the same extent as if each individual publication, database entry (e.g. Genbank sequences or Gene ID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or Gene ID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims. The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

What is claimed is:

1. A method for treating or preventing Barrett's esophagus (BE) and related conditions in a mammal, the method comprising orally applying an antimicrobial or antiseptic rinse at least once daily to the mammal,
wherein the antimicrobial or antiseptic rinse comprises chlorhexidine.

2. The method of claim 1, wherein the related conditions are selected from the group consisting of esophageal cancer, esophageal adenocarcinoma, gastroesophageal reflux disease (GERD), and indigestion, and eosinophilic esophagitis.

3. The method of claim 1, further comprising administering an effective amount of one or more probiotics or prebiotics.

4. The method of claim 1, wherein the mammal is human.

5. The method of claim 1, wherein the antimicrobial or antiseptic rinse is applied for at least two weeks.

6. The method of claim 1, wherein the antimicrobial or antiseptic rinse is continued until a desired esophageal and/or salivary microbiome is achieved.

7. The method of claim 3, wherein the one or more prebiotics or probiotics comprise a live bacterial strain.

8. The method of claim 3, wherein the one or more prebiotics or probiotics comprise a buffering agent selected from the group consisting of sodium bicarbonate, milk, and yogurt.

* * * * *